United States Patent [19]

Clark

[11] Patent Number: 4,978,724

[45] Date of Patent: Dec. 18, 1990

[54] METHOD OF PREPARING DERIVATIZED POLYSTYRENE FOR SPECTROSCOPIC STUDIES

[75] Inventor: Brian R. Clark, Mission Hills, Calif.

[73] Assignee: Applied ImmuneSciences, Inc., Menlo Park, Calif.

[21] Appl. No.: 948,418

[22] Filed: Dec. 30, 1986

Related U.S. Application Data

[63] Continuation of Ser. No. 555,038, Nov. 23, 1983, abandoned.

[51] Int. Cl.$^5$ .............................. C08F 8/34; C08F 8/24
[52] U.S. Cl. .................................... 525/350; 435/180;
436/531; 525/343; 525/359.3; 525/375;
525/376; 525/378; 525/384
[58] Field of Search .............. 525/333.3, 333.4, 359.3,
525/359.4, 350, 375, 376, 378, 384, 343

[56] References Cited

U.S. PATENT DOCUMENTS

| | | | |
|---|---|---|---|
| 2,404,722 | 7/1946 | Houtz | 524/84 |
| 2,460,579 | 2/1949 | Houtz | 524/84 |
| 4,031,038 | 6/1977 | Grinstead | 525/333.4 |
| 4,087,599 | 5/1978 | Roe | 525/333.4 |
| 4,089,815 | 5/1978 | Reiter | 525/333.4 |
| 4,315,998 | 2/1982 | Necker5s | 525/333.4 |

Primary Examiner—Christopher Henderson
Attorney, Agent, or Firm—Bertram I. Rowland

[57] ABSTRACT

Molded articles formed of polystyrene or other polymers containing an aromatic moiety can be derivatized on the surface of the article by subjecting the molded article to a chemical reaction wherein the reaction media utilizes tetramethylsulfone as the reactant solvent and a suitable substituent group which is substituted on to the aromatic moiety of the polystyrene or other polymer by electrophilic substitution. By choosing the substituent group to further include a leaving group, further substitution of the primary substituent can be effected normally by nucleophilic substitution reaction. In this way, biologically important molecules can be attached to a polystyrene or other aromatic containing polymer without effecting certain properties of the molded article such as its optical or spectroscopic clarity.

2 Claims, No Drawings

# METHOD OF PREPARING DERIVATIZED POLYSTYRENE FOR SPECTROSCOPIC STUDIES

CROSS REFERENCE TO RELATED APPLICATION

This application is a continuation of Ser. No. 555,038, filed Nov. 23, 1983 now abandoned.

BACKGROUND OF THE INVENTION

This invention is directed to supports utilized for making spectroscopic measurements and other studies which utilize polystyrene or other aromatic containing polymers which are derivatized in such a manner so as to maintain the spectroscopic clarity of the support.

Polystyrene is one of the most used of all polymers. It is utilized either as pure polystyrene or in conjunction with a copolymer. Further, derivatives of polystyrene are known, such as chloromethylated polystyrene.

Polystyrene and its copolymers are soluble in most of the normal organic solvents with the exception of the lower alcohols. Other solvents swell or gel polystyrene and copolymers of polystyrene. The swelling action of many solvents on polystyrene allows for the use of polystyrene as the support matrix for resins utilized for chromotography, ion exchange and the like.

Appropriate functional groups can be introduced into the aromatic rings of the polystyrene by one of two methods. The first is the actual polymerization of monomers which incorporate these functional groups. U.S. Pat. No. 3,872,067 describes a process for preparing a chloromethylated polystyrene divinyl benzene copolymer utilizing appropriate polymerization of the preformed chloromethylated polystyrene monomer.

For preparing derivatives of polymerized polystyrene. it is necessary to swell the polystyrene matrix such that pores and the like are formed in the polystyrene matrix allowing for introduction of the appropriate functional groups within the interior of the polystyrene bead or the like. U.S. Pat. No. 3,956,219 describes this process and discusses the problems with regard to the same. In this patent the polystyrene is being substituted with certain peptide functionalities which have different solvent properties compared to the polystyrene. As the patent describes, in utilizing certain solvents such as methylene chloride, the polystyrene is extended, but the peptide functionalities are not soluble in this solvent or other similar solvents. The solution of U.S. Pat. No. 3,956,219 is in the use of N-methyl-2-pyrrolidone which acts both as a swelling agent for the polystyrene and as a solvent for the peptide groups.

U.S. Pat. No. 3,860,486 describes the use of polymethylated styrene as a matrix for insolubilizing certain enzymes by reacting the chloromethyl groups with 2,5-dioxo-4 oxazolidine. The water soluble enzymes react with the oxazolidine group to insolubilize the same. This patent is characteristic of certain procedures wherein biological molecules can be manipulated by the absorption, attachment or reaction of the same with a suitable insoluble matrix such as a derivatized polymer or the like.

Both U.S. Pat. Nos. 3,974,110 and 3,995,094 discuss Freidel-Crafts substitution reactions for the introduction of chloromethyl groups onto the aromatic ring of polystyrene. In the body of U.S. Pat. No. 3,995,094 discussion is set forth as to problems with regard to solvents which can be utilized for such Freidel-Crafts modifications of polystyrene. Organic solvents such a benzene, toluene, xylene and the like themselves would undergo the halomethylation reaction and thus are not useful as solvents. The alcohols, diols and the like deactivate the normal Lewis acids utilized as catalysts in these reactions. Noted as acceptable solvents for the halomethylation of polystyrene are carbon disulfide and nitroalkanes and nitroaranes and the lower haloalkanes.

The above patents are directed to the reactions specified therein with little consideration given to the actual final use of the polystyrene article. Thus, while carbon disulfide and chloroform might be suitable for Freidel-Crafts reactions on polystyrene, they could not be utilized if a polystyrene article was to be maintained in the same physical form after the reaction as it was before the start of the reaction.

U.S. Pat. No. 4,226,958 converts polystyrene to bromopolystyrene by bromination with bromine in carbon tetrachloride. The brominated polystyrene is then further reacted in other solvents to form certain organoarsenic derivatives of the polystyrene. Again, as with the reactions discussed above, during the bromination step utilizing carbon tetrachloride little consideration is given to maintaining certain physical properties of the polystyrene such as optical clarity, optical surfaces and the like during the reaction thereon.

Because polystyrene can be derivatized such as by the formation of chloromethylated polystyrene, and because it is a transparent solid, it has been determined that polystyrene, polystyrene plus other copolymers, or other aromatic moiety containing polymers which also are optically clear, could be useful for support mediums for certain spectroscopic studies. However, in order to so utilize these polymers for this purpose, consideration must be given to maintaining the optical clarity of these supports and preventing solvation, geling, swelling, etching, or other physical changes to the support medium during any reaction on the polystyrene itself or on subsequent derivatives of polystyrene. It is to this end that this invention is directed.

BRIEF DESCRIPTION OF THE INVENTION

It has been determined that, by reacting polystyrene with suitable chemical reactants under certain conditions the optical properties of a polystyrene article can be maintained. Furthermore, it has been determined that by reacting polystyrene with certain reactants in the presence of certain solvents that reaction of the polystyrene in a preformed article can be limited to the surface of the article. This avoids derivatizing the total matrix of the polystyrene such that upon further reaction of the derivatized polystyrene with large molecules which are unable to penetrate the polystyrene matrix, the derivative groups to which the large molecules are attached also do not interfere with the spectroscopic properties of the polystyrene article.

In view of this it is a broad object of this invention to provide a process for initially introducing a functionality onto polystyrene or other aromatic group containing polymers utilizing a solvent system which maintains the optical integrity of the polystyrene and by not solvating, swelling, gelling or otherwise interacting with the main body of the polymetric article, limits the derivation of the aromatic moieities of the polymer to the surface of the article. It is a further object of this invention to provide support surfaces formed of polystyrene or other like polymers which contain aromatic moieties which are useful in supporting or holding biologically interesting molecules or useful in attaching those molecules to a support surface such that the molecules can be further derivatized and/or spectroscopically tagged, i.e. made to flouresce and the like, in order to study these molecules.

These, and other objects, as will be evident from the remainder of this specification are achieved in a process of derivatizing only the surface of an article formed of a polymer containing an aromatic moiety by introducing a substituent group onto said aromatic moiety which comprises: contacting said surface of said article with a reaction mixture wherein said reaction mixture contains tetramethylene sulfone as the solvent of said reaction mixture and further includes a reagent containing said substituent group; maintaining said reaction mixture in contact with said surface of said article to introduce said substituent group onto at least a portion of said aromatic moieties of said polymer located on said surface of said article; isolating said article from said reaction mixture.

The article of the preceding paragraph can be additionally reacted on wherein said substituent group is chosen from the group consisting of halo, haloalkyl, acyl and formyl and further including; contacting said isolated article with a further reaction mixture wherein said further reaction mixture contains one of the group consisting of tetramethylene sulfone, dimethyl disulfoxide or aqueous media as the solvent in said further reaction mixture and said further reaction mixture includes a reagent containing a nucleophile; maintaining said further reaction mixture in contact with said surface of said article to substitute the halo function of said halo and alkyhalo substitutent groups and the keto function of said formyl and said acyl substituted groups with said nucleophile; isolating said article from said further reaction mixture.

Additionally, the objects of the invention can be achieved in an article formed of polystyrene wherein on the surface of the article includes haloalkyl or acyl substitution groups, a process of derivitizing the halo alkyl or acetyl groups without destroying the spectroscopic clarity of the article which comprises: contacting said article with a reaction mixture wherein said reaction mixture contains one of the group consisting of tetramethylene sulfone, dimethyl sulfoxide or aqueous media as the solvent of the reaction mixture and further includes a reagent containing a nucleophile; maintaining said further reaction mixture in contact with said surface of said article to substitute the halo function of said halo and said haloalkyl substitutent groups and the keto function of said formyl and said acetyl substituent groups with said nucleophile; isolating said article from said reaction mixture.

By initially derivatizing polystyrene or a like aromatic containing polymer in the presence of tetramethylene sulfone, by essentially an electrophilic substitution reaction, the aromatic moiety of the polystyrene or other aromatic containing polymer is derivatized with a functional group on the surface of an article, while still maintaining the integrity of the article with respect to certain properties such as optical or spectroscopic clarity. Further, by not swelling, gelling or otherwise expanding the polymeric matrix, the dimensions of the article can be maintained within an acceptable tolerance. The group which is electrophilically substituted onto the aromatic moiety of the polystyrene or other aromatic containing polymers can be further reacted on if it is chosen so as to include a site of reactivity. Thus, the keto function of the formyl or acetyl groups is susceptible to further reaction utilizing known standard reaction sequences. Further, the halo groups on a halopolystyrene or similar aromatic moiety containing polymer or a haloalkyl polystyrene or other aromatic moeity containing polymer is susceptible to substitution reactions also in a known manner. However, in undertaking these further reactions, consideration must again be given to maintaining the optical or spectroscopic integrity of the basic article.

For the initial substitution of the aromatic ring, not only must solvent effects of the polystyrene or other aromatic containing polymer be considered in order to avoid distortion of the basic properties of the article, but further consideration with regard to the solvent must be given to the reaction itself such that the solvent does not interfere with the basic reaction. As such, solvents which themselves can serve as reacting species are precluded and solvents such as Lewis bases, alcohols, aqueous solvents, ethers and the like which would serve as terminators or catalytic poisons for the basic reaction, must also be avoided.

In subsequently reacting the substituted polystyrene or other aromatic polymer with a further reaction, the considerations with regard to the solvent effects on the article itself must be maintained. However, the nature of the solvent being reactant itself is modified from the original electrophilic substitution of the aromatic moiety.

For the initial electrophilic substitution reaction, tetramethylene sulfone is the solvent chosen. For the additional reactions further solvents in addition to tetramethylene sulfone can be utilized. These include dimethyl sulfoxide and aqueous based reaction media.

Preferredly, once the original substituent group is introduced onto the polystyrene or other aromatic moiety containing polymer, the second substituent group then reacted with the first substituent group would be a difunctional substituent group such that the first functionality of this second group would react with the first, or primary substituent attached to the polystyrene or other aromatic moiety of the polymer with the further substituent then available as an additional reaction site to attach other groups to the article. These other groups would generally be selected from biologically interesting molecules, such as peptides, proteins, enzymes, antibiotics, sugars, nucleic acids and the components thereof, starches and lipids, and further cells, cell membranes, viral proteins and the like might also be attached by utilizing binding sites on the surface of the cell, cell membranes, viral proteins and the like to react with the further functionality of the difunctional subsequent group which is attached to the primary substituent group on the polystyrene or aromatic moiety of a similar polymer.

Agents which are capable of interacting with biologically interesting molecules, such as flourescing agents, dyes and the like, can additionally be reacted with the biologically interesting molecule attached to the article in the same solvent systems as were noted for attaching the biologically interesting molecule itself.

DETAILED DESCRIPTION OF THE INVENTION

Insofar as tetramethylene sulfone (TMS) is an excellent solvent for Lewis acid catalysts such as stannic bromide and the like, Freidel-Crafts acylations and alkylations can be utilized to derivatize polystyrene or other polymer containing an aromatic moeity. Thus, typical Freidel-Crafts alkylation reactions can be run such as attaching a bromomethyl group to polystyrene utilizing stannic bromide and bromomethylmethyl ether and typical Freidel-Crafts acylations can be run utilizing the same Lewis acid, stannic bromide, and acetyl bromide to acetylate the aromatic ring of polystyrene. In a like manner, higher haloalkyls and higher acetyls can be introduced.

For both alkylations and acylations aside from stannic bromide or chloride other Lewis acids such as boron trifluoride, aluminum chloride, ferric chloride, zinc chloride and the like can also be considered. Formylation of the polystyrene could be effected utilizing formylation reactions such as carbene intermediates formed in a Reimer-Tiemann reaction or, alternately, Gattermann-Koch or Vilsmeyer reaction can be utilized to introduce the formyl group onto the aromatic moiety of the polymer. Normally, other activating groups could also be present on the aromatic moiety to facilitate the formylation reactions such as using a phenolic or xylene based polymer.

For the introduction of a nitro, sulfonyl or diazo group onto the polystyrene or other aromatic moiety of a basic polymer, a standard electrophilic substitution reaction would be undertaken.

Insofar as higher aromatic compounds such as napthalene, anthracene and the like are also susceptible to these electrophilic reactions, polymers which incorporate these as aromatic moieties would also be susceptible to these electrophilic substitutions in order to derivatize the same only on the surface of an article formed of these polymers without distortion of the article by polymetric swelling, gelling, solvation or the like.

For subsequent reactions on the article once the primary substituent group is located thereon, typical nucleophilic reactions are utilized. As such, the halogen of a halo or haloalkyl primary substituent group can be easily displaced by nucleophilic substitution utilizing amines, alcohols, thiols, hydrazines, phenols, anilines and the like. Additionally, water, ammonia, hydrogen sulfide, disulfides, phosphates and other typical reactants could be utilized.

Alternately, biologically important molecules such as peptides, proteins, enzymes, antibiotics, sugars, nucleosides, nucelotides, nucleic acids, starches and lipids including steroids, terpines, fatty acids, phosphotides, glycolipids, aliphatic alcohols and waxes could also be utilized by taking advantage of a reactant group on these molecules to interact with the reactant group on the primary substituent attaching to the aromatic moiety of the polymer on the surface of the article.

Normally, for laboratory identification, medical testing purposes and the like, a difunctional group would be attached to the primary substituent utilizing a first functionality of the difunctional group to attach to the primary substituent and leaving a second functionality of the difunctional group open so as to provide a further reactant site for attachment of the above biologically important molecules. Any typical difunctional group containing amines, alcohols, thiols, hydrazines, disulfides and the like could be utilized. Also, molecules which can serve as a biological indicators either by a particular biological reactivity or by exhibiting a chemical or physical effect such as fluorescence or color change could further be attached.

In all of the above, standard chemical reaction conditions would be maintained with the exception that all reactions, whether they are the introduction of the primary substituent on to the aromatic moiety of the polymer or subsequent additions to this primary substituent are performed in solvent systems which do not gel, swell or solvate the polymer such that the integrity of the article formed of the polymer with regard to at least optical and/or spectroscopic properties is maintained and is not detracted from. Excluded from consideration therefore as solvents are any solvents which swell, gel, solvate or otherwise interact with the polymer and which further interfere with the chemical reaction being performed on the polymer.

As representative examples, the following examples are mentioned, with reference being made to the accompanying flow charts. In the flow charts the polymeric backbone is represented by the comb like symbol.

Referring to Scheme 1, the following examples were performed.

EXAMPLE 1

BROMOMETHYL POLYSTYRENE (II)

1.2 mls (9.1 moles) of warm (40°) $SnBr_4$ is added to 8.0 mls of warm (40°) tetramethylene sulfone (TMS) in a 12 ml screw top centrifuge tube. The tube was capped with a Teflon capped screw cap and the contents were mixed by inverting several times. To this, 0.8 mls (9.8 moles) of bromomethylmethyl ether was added, followed by mixing. 50 microliters of the resultant straw colored solution was added to each well of a polystyrene (I) microtiter plate. The reaction was allowed to run at room temperature for 18 hours, at which time the content of each of the wells was aspirated and the plate was rinsed thoroughly with anhydrous methanol and allowed to dry at room temperature to yield the polystyrene microtiter plate being derivatized with bromomethyl groups (II) at its surface within each of the wells.

EXAMPLE 2

Acetyl Polystyrene (III) 1.0 mls of $SnBr_4$ was added to 9.0 mls of TMS as per Example 1. To this was added 0.2 mls of acetyl bromide followed by mixing. As with Example 1, 50 microliters of the solution was added to each of the wells of the polystyrene microtiter plate and the reaction allowed to proceed for 18 hours at room temperature. After drying, the plates were rinsed with methanol and dried to yield the polystyrene microtiter plate derivatized with acetyl groups (III) on its surface in each of the wells.

EXAMPLE 3

A bromomethylated polystyrene microtiter plate (III) derivatized as per Example 1, above, was utilized for this Example. 1.5 gm of dithiothreitol was dissolved in 10 ml of TMS and 100 microliters of this was added to each of the wells of the bromomethylated microtiter plate (II). The reaction was allowed to proceed for 3 hours at room temperature at which time each of the wells was aspirated to remove the contents therein and thoroughly washed with methanol to yield each of the wells derivatized with 1-methyldithiothreitol (IV).

EXAMPLE 4

(a) The same reaction as per Example 3 above was rerun utilizing 0.1 molar sodium bicarbonate as the reactant solvent. As per Example 3, the wells were aspirated after 3 hours and thoroughly rinsed with anhydrous methanol to also yield the microtiter plates derivatized with 1-methyldithiothreitol (IV).

(b) The same reaction was repeated utilizing DMSO as the solvent to also yield Compound IV.

EXAMPLE 5

A microtiter plate derivatized with Compound IV as per Examples 3 or 4 was further treated by the addition of the enzyme beta-galactosidase. A 1mg/ml solution of E. Coli beta-galactosidase was diluted 1:200 with 0.1 Molar sodium bicarbonate containing 0.5% tween 20 added to percent nonspecific attachment of the enzyme. 75 microliters of this solution was added to each of the wells of the microtiter plate derivatized with Compound III. The wells were incubated for 2 hours at room temperature at which time they were then aspirated and rinsed with 0.1 Molar sodium bicarbarbonate/0.5% tween 20 to yield microtiter plates having the beta-galactosidase V attach via a disulfide bond to the dithiothreiotol which in turn was attached by a thioether bond to the methyl polystyrene.

EXAMPLE 6

The presence of the beta-galactosidase (V) of Example 5 in each of the wells of the microtiter plate was demonstrated by adding 150 microliters of a filtered saturated solution of 4-methylumbelliferone beta-D-galactopyranoside (VI) in phosphate buffer saline (PBS) to each of the wells. The polystyrene microtiter plate was irradiated with UV light and photographed to demonstrate presence of the Beta-D-galactosidase attached to the wells. This was demonstrated by fluorescence caused by cleavage by the beta galactosidase of the bond between the Beta-D-galactopyraniside and the 4-methylumbelliferone compound to yield Compound V which fluoresces as opposed to the lack of fluorescence for the parent 4-methylumbelliferone Beta-D-galactopyranoside.

EXAMPLE 7

In order to demonstrate the attachment of the Beta-D-galactosidase of Example 5 above, a polystryene microtiter plate derivatized so as to contain Compound II as per Example 1, above, was further reacted with 2-mercaptoethanol in TMS at room temperature for 3 hours. Following the reaction, the contents of each of the wells of the microtiter plate were aspirated and washed thoroughly with methanol to yield a microtiter plate derivatized with methyl-2-hydroxyethylthioether, Compound VIII.

EXAMPLE 8

A microtiter plate derivatized with methyl-2-hydroxyethylthioether Compound VIII, was reacted with conditions identical to Example 5 above, followed by conditions identical to Example 6 above. Upon exposure to UV light, no fluorescence was noted, indicating lack of attachment of the Beta-D-9alactosidase to the hydroxyl group of the methyl-2-hydroxyethylthioether as opposed to the coupling of the Beta-D-9alactosidase to the thio ether moiety of the dithiothreiotol derivatized Compound IV above.

In reference to Scheme 2 the following examples were performed.

EXAMPLE 9

The acetylated polystyrene plates, Compound III above, were treated with dansyl hydrazine in TMS in the presence of acetic acid at room temperature for 3 hours. Following aspiration, the wells of the plates were rinsed with methanol to yield Compound IX the dansyl hydrazine of the acetylated polystyrene (III). When the microtiter plates derivatized with Compound IX were exposed to UV light, fluorescence was noted indicating attachment of the dansyl group through a hydrazone linkage to the polystyrene.

EXAMPLE 10

As a control for Example 9, an identical reaction was run utilizing an excess of succinic dihydrazide to form Compound X.

EXAMPLE 11

Compound X was incubated in TMS in the presence of acetic acid for 2 hours at room temperature with dansyl hydrazine and after aspiration of the wells of the microtiter plates the plates were subjected to UV light with no fluorescence seen, indicating lack of attachment of dansyl hydrazine to the microtiter plate. This is indicative of prior attachment of the succinic dihydrazide to the acetyl group on the surface of the microtiter plate such that the acetyl functionality on the derivatized polystyrene was no longer available for the reactivity with dansyl hydrazine to form a fluorescent species.

Referring now to Scheme 3, the following examples are shown for illustrative purposes of further potential utilization of the derivitized microtiter plates of the invention.

EXAMPLE 12

Utilizing tetramethylsulfone, dimethyl sulfoxide or aqueous media, the following reactions could also be run in a manner analagous to that shown in Example 3, utilizing the reagent shown for the specific flow schemes. By reacting with ammonia, Compound XIIa the aminomethyl derivative of polystyrene would be obtained. Likewise, by reacting with water, the hydroxymethyl Compound XIIb would be the result; by reacting with hydrogen sulfide the methylthiol Compound XIIc would be obtained; by reacting with hydrazine, the methylhydrazino Compound XIId would be obtained; by reacting with the difunctional compound aminomethylmercaptan, Compound XIIe, the 2-aminoethylmethylthiol ether difunctional compound, would be obtained; by reacting with a further difunctional compound, beta-mercapto acetic acid, Compound XIIf would be obtained; and by reacting with an appropriate peptide such as the dipeptide tyrosylcysteine the tyrosylcysteine methylthiolether Compound XIIg would be obtained; and in a like manner, by reacting with an appropriate alcoholic function such as an appropriate nucleoside, Compound XIIh would be obtained.

EXAMPLE 13

In a like manner to Example 3 above, the bromethylated polystyrene (II) could be reacted with p-acetylphenol to yield Compound XIII.

EXAMPLE 14

Utilizing the same reaction conditions as were utilized for Example 9, Compound XIII could be treated with hydrazine to yield the hydrazone compound, Compound XIV.

EXAMPLE 15

The hydrazone derivative Compound XIV could then be further treated with gluceronic acid lactone to yield the 1,4 lactone Compound XV.

EXAMPLE 16

The 1,4 lactone derivative XV could be treated in appropriate aqueous media with various biologically interesting species capable of opening the 1,4,1actone ring, such as proteins and the like to yield the attached protein Compound XVI.

As per certain of the above Examples, it is seen that by utilizing electrophilic substitution reactions, such as Examples 1 and 2, a first or primary substituent group is attached to the polystyrene. Further, by utilizing nucleophilic substitution reactions, as for example Example 9, an additional substituent is then attached to the primary substituent to attach this additional substituent onto the matrix of the polystyrene. Alternately, by utilizing difunctional substituents as nuceophiles for reaction with the primary substituent, as for example Example 4, a first functionality of the bifunctional substituent is attached to the primary substituent leaving the second functionality open for further reaction as per Example 5, wherein the terminal sulfhydro group is then reacted with a biologically important molecule, i.e. an enzyme, to ultimately attach this enzyme to the polystyrene. All of the reaction sequences are done in such a manner that the basic polystyrene support is maintained optically clear and is not etched, swelled, gelled, softened or otherwise physically altered, such that this support surface is suitable for conducting spectroscopic or other suitable measurements thereon as per the fluorescence achieved in Example 6 wherein the enzyme attached to the polystyrene support structure is able to cleave the glucosidic bond between the pyranoside sugar and the fluorescent 4 methylumbelliferone.

By choosing the appropriate substituents utilizing the reaction schemes outlined above, biologically important molecules can ultimately be attached to the polystyrene utilizing reactive functionalities present on these biologically important molecules, such as hydroxyl groups, amine groups, sulfhydro groups, disulfide groups, acid functionalities, amino acid functionalities and the like.

It is further evident that cell membranes, viral protein coats or even whole cells could likewise be attached to the polystyrene support structure by appropriate chemical bridges formed between them and the polystyrene.

Assay techniques are useful in studying reactions, reaction rates and the like of biologically important molecules. Prior assay techniques relied on physical absorption between the biologically important species and the assay plate or support surface. This oftentimes led to erroneous data generation because of dilution of the biologically important molecule off of the the assay plate due to the transitory nature of the physical absorption of the biologically important molecule or specie on to the assay plate.

This problem is eliminated with the present invention in that the biologically important molecule or species are chemically attached to the assay plate and do not rely on physical absorption of the same to maintain them in association with the assay plate. As was noted in Example 5 above, tween 20, a detergent, was utilized in the Example to prevent physical absorption of the biological species or other species on to the assay plate such that the molecules or other physical entities of the biologically important species are only chemically attached to the assay plate and are not simply physically absorbed thereon. By the use of the detergent tween 20 physical absorption is prevented and as such, the resulting assay plate exhibits a high degreee of specificity and reproducibility and does not suffer from a gradual decline or loss of the molecules or biological entities off of the plate during the actual assay procedures.

SCHEME #1

SCHEME #1

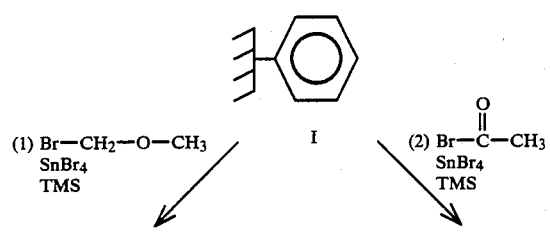

-continued
SCHEME #1
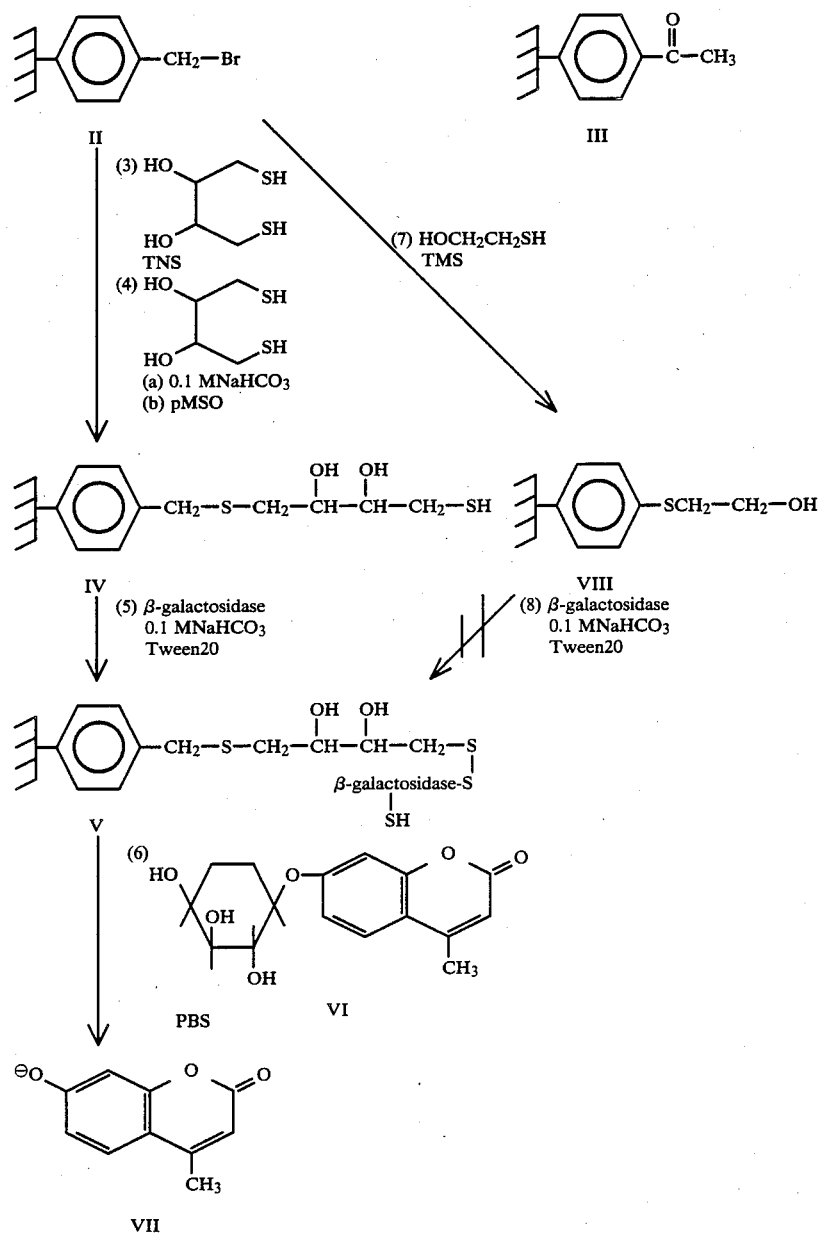
SCHEME #2
SCHEME #2
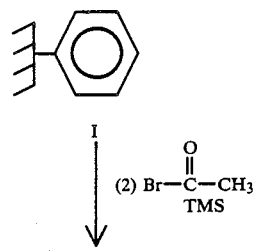

-continued
SCHEME #2
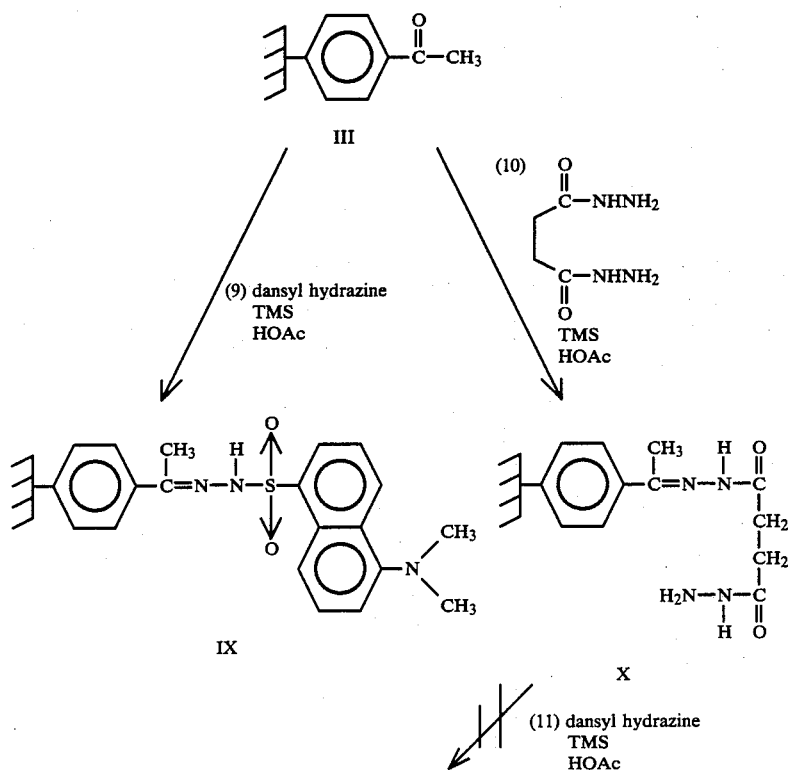
SCHEME #3
SCHEME #3
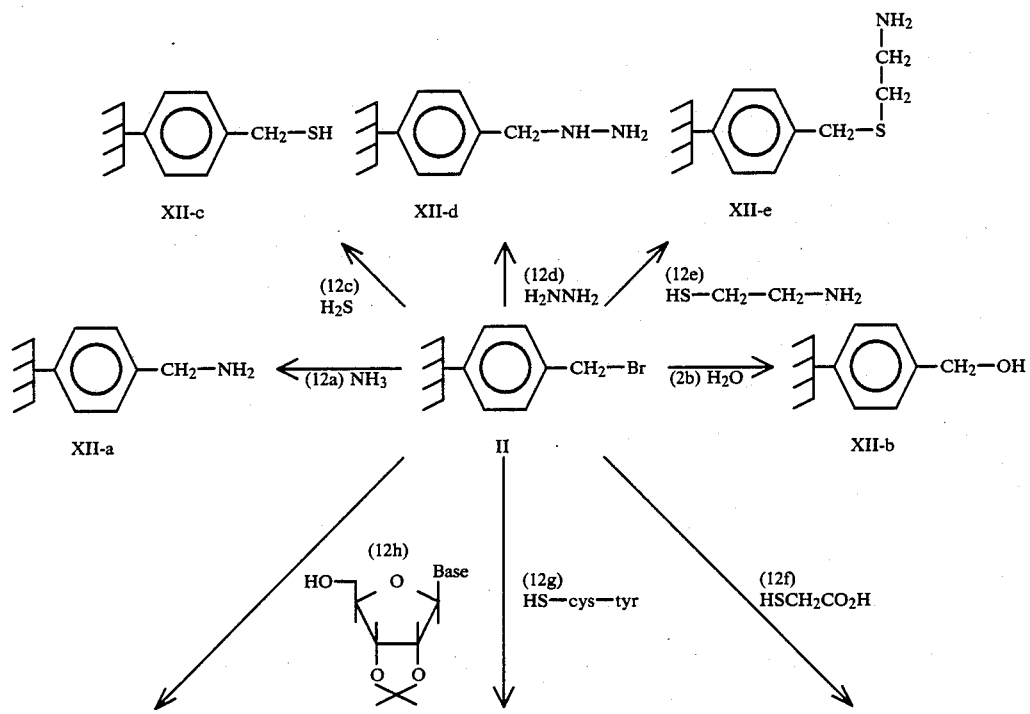

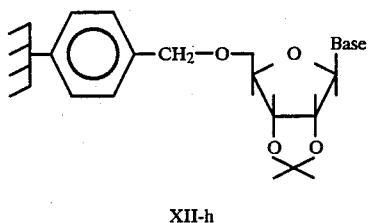
XII-h
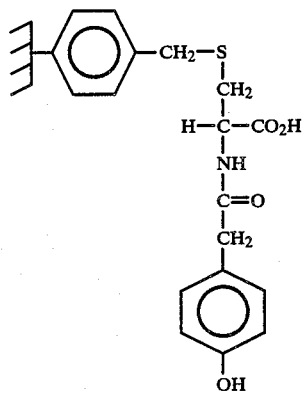
XII-g
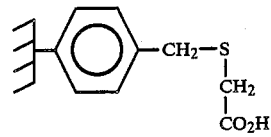
XII-f
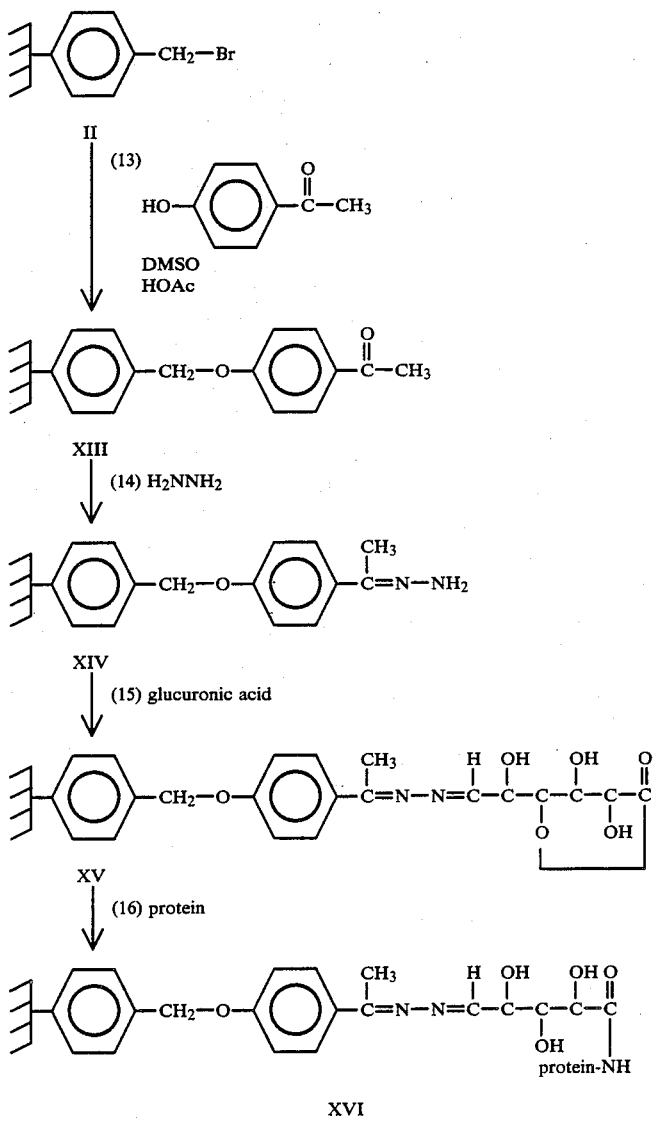
I claim:
1. A method for producing an article formed from polystryene and functionalized on its surface by substitution with an electrophilic reagent followed by reaction with an additional reagent, said method comprising:

reacting said surface with a reaction mixture comprising said electrophilic reagent in tetramethylene sulfone solvent under conditions and for a time sufficient for said electrophilic reagent to react with said aromatic monomer on the surface of said article to covalently bond substituent groups to said surface to provide a first substituted article;

reacting said first substituted article with a second reaction mixture comprising a nucleophilic reagent in tetramethylene sulfone, dimethyl sulfoxide, water or combination thereof under conditions and for a time sufficient for said nucleophilic reagent to react with said substituent; and isolating said article from said second reaction mixture.

2. A method according to claim 1, wherein said nucleophile is water, ammonia, hydrogen sulfide, an alcohol, an amine, a hydrazine, a mercaptan, a phenol, lipid, or combination thereof.

* * * * *